United States Patent
Hirokami

(10) Patent No.: US 10,047,229 B2
(45) Date of Patent: Aug. 14, 2018

(54) POWDER COATING COMPOSITION AND COATED ARTICLE

(71) Applicant: Shin-Etsu Chemical Co., Ltd., Tokyo (JP)

(72) Inventor: Munenao Hirokami, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/201,855

(22) Filed: Jul. 5, 2016

(65) Prior Publication Data

US 2017/0009081 A1 Jan. 12, 2017

(30) Foreign Application Priority Data

Jul. 6, 2015 (JP) .................................. 2015-135344

(51) Int. Cl.
| | |
|---|---|
| C09D 5/03 | (2006.01) |
| C08G 18/79 | (2006.01) |
| C09D 167/00 | (2006.01) |
| C08G 18/28 | (2006.01) |
| C07F 7/18 | (2006.01) |
| C08K 5/5455 | (2006.01) |

(52) U.S. Cl.
CPC .............. *C09D 5/03* (2013.01); *C07F 7/1868* (2013.01); *C08G 18/289* (2013.01); *C08G 18/792* (2013.01); *C09D 167/00* (2013.01); *C08G 2150/20* (2013.01); *C08K 5/5455* (2013.01)

(58) Field of Classification Search
CPC ....................................................... C09D 5/03
See application file for complete search history.

(56) References Cited

U.S. PATENT DOCUMENTS

| | | |
|---|---|---|
| 5,266,657 A | 11/1993 | Hammerton et al. |
| 5,393,846 A | 2/1995 | Hammerton et al. |
| 5,932,678 A | 8/1999 | Meier et al. |
| 6,281,322 B1 | 8/2001 | Groth et al. |
| 6,288,198 B1 * | 9/2001 | Mechtel ............... C08G 18/289 |
| | | 106/287.11 |
| 9,404,011 B2 | 8/2016 | Groenewolt et al. |
| 2013/0196072 A1 | 8/2013 | Groenewolt et al. |

FOREIGN PATENT DOCUMENTS

| | | |
|---|---|---|
| EP | 0 516 375 A2 | 12/1992 |
| EP | 1 006 132 A1 | 6/2000 |
| JP | 5-156178 A | 6/1993 |
| JP | 9-255876 A | 9/1997 |
| JP | 10-17660 A | 1/1998 |
| JP | 2000-169790 A | 6/2000 |
| JP | 2001-294805 A | 10/2001 |
| JP | 2011-88083 A | 5/2011 |
| JP | 2013-527867 A | 7/2013 |
| WO | WO 00/75212 A1 | 12/2000 |

OTHER PUBLICATIONS

Extended European Search Report, dated Sep. 9, 2016, for European Application No. 16177731.3.
Ni et al., "Siloxane Functionalized Isocyanurate Coatings," Polymer Preprints, vol. 39, No. 1, Mar. 1998, pp. 367-368.

* cited by examiner

*Primary Examiner* — Michael F Pepitone
(74) *Attorney, Agent, or Firm* — Birch, Stewart, Kolasch & Birch, LLP

(57) ABSTRACT

A powder coating composition comprising a specific organosilicon compound forms a coating which exhibits satisfactory water-loading resistant performance.

5 Claims, No Drawings

POWDER COATING COMPOSITION AND COATED ARTICLE

CROSS-REFERENCE TO RELATED APPLICATION

This non-provisional application claims priority under 35 U.S.C. § 119(a) on Patent Application No. 2015-135344 filed in Japan on Jul. 6, 2015, the entire contents of which are hereby incorporated by reference.

TECHNICAL FIELD

This invention relates to a powder coating composition is capable of forming a coating having water-loading resistant performance.

BACKGROUND ART

Powder coating compositions are regarded attractive as low-pollution paint because no organic solvents volatilize into the atmosphere during coating operation. In particular, polyester resin based powder coating compositions comprising a polyester resin and a crosslinker are known applicable to metal articles. As the crosslinker used therein, triglycidyl isocyanurate (TGIC) and blocked polyisocyanates are well known. The use of TGIC is undesirable because of its skin irritation and toxicity. The blocked polyisocyanates have the problems that the blocking agents are substances regulated by the Pollutant Release and Transfer Register (PRTR), and blocked polyisocyanates become volatile organic compounds (VOC) if released during bake of a coating.

From the environmental aspect, attention is paid to hydroxyalkylamide compounds, which are curing agents free of blocking agents. For example, JP-A H05-156178 and JP-A H10-017660 disclose powder coating compositions comprising hydroxyalkylamide compounds. However, polyester resin-based powder coating compositions using hydroxyalkylamide compounds as the curing agent are less adhesive, failing to form coatings having satisfactory water-loading resistant performance.

CITATION LIST

Patent Document 1: JP-A H05-156178 (USP 5266657)
Patent Document 2: JP-A H10-017660

DISCLOSURE OF INVENTION

An object of the invention is to provide a powder coating composition having satisfactory water-loading resistant performance, and a coated article using the same.

The inventor has found that a powder coating composition is obtained by combining a resin, typically polyester resin with an organosilicon compound having the general formula (1), especially general formula (2), below, and that the powder coating composition is resistant to boiling water and moisture, and exhibits satisfactory water-loading resistant performance.

In one aspect, the invention provides a powder coating composition comprising (A) an organosilicon compound having the general formula (1).

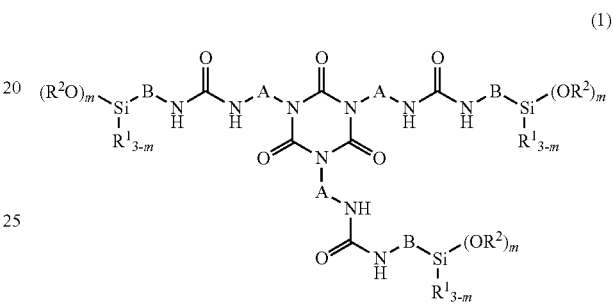

(1)

Herein $R^1$ is each independently a $C_1$-$C_{10}$ alkyl or $C_6$-$C_{10}$ aryl group, $R^2$ is each independently a $C_1$-$C_{10}$ alkyl or $C_6$-$C_{10}$ aryl group, A is a $C_1$-$C_{20}$ divalent hydrocarbon group, B is a $C_1$-$C_{20}$ divalent hydrocarbon group, and m is an integer of 1 to 3.

Preferably, the organosilicon compound has the general formula (2):

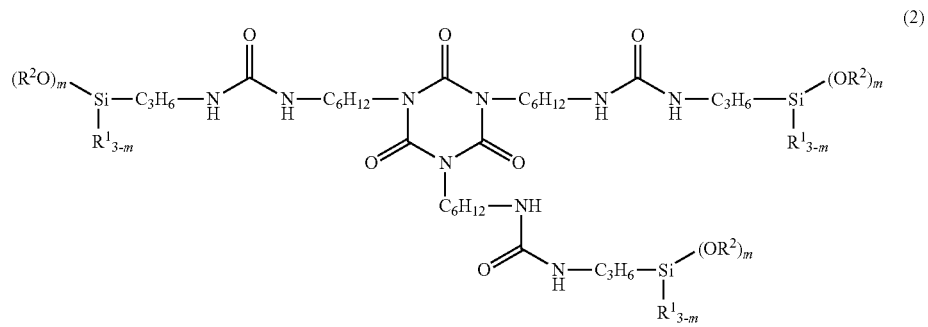

(2)

wherein $R^1$, $R^2$, and m are as defined above.

The powder coating composition may further comprise (B) a carboxyl-containing polyester resin and/or (C) a β-hydroxyalkylamide compound.

Also contemplated herein is a coated article obtained by coating a substrate with the powder coating composition defined above.

Further, the invention provides an organosilicon compound having the general formula (1) above.

Preferably, the organosilicon compound has the general formula (2) above.

Advantageous Effects of Invention

The powder coating composition comprising a specific organosilicon compound exhibits satisfactory water-loading resistant performance.

DESCRIPTION OF PREFERRED EMBODIMENTS

As used herein, the notation (Cn-Cm) means a group containing from n to m carbon atoms per group. The term "silane coupling agent" is encompassed in the term "organosilicon compound." In the chemical formulae, Me stands for methyl, and Et for ethyl.

The powder coating composition of the invention is defined as comprising (A) an organosilicon compound having the general formula (1).

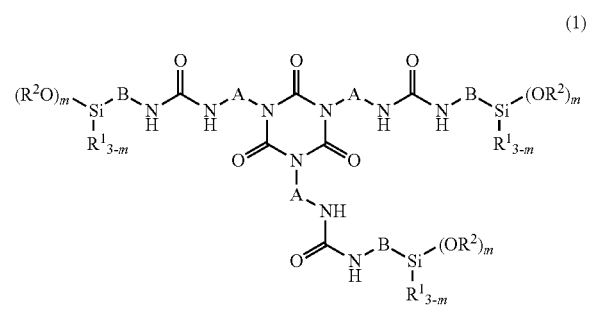

(1)

Herein $R^1$ is each independently a $C_1$-$C_{10}$ alkyl or $C_6$-$C_{10}$ aryl group, $R^2$ is each independently a $C_1$-$C_{10}$ alkyl or $C_6$-$C_{10}$ aryl group, A is a $C_1$-$C_{20}$ divalent hydrocarbon group, B is a $C_1$-$C_{20}$ divalent hydrocarbon group, and m is an integer of 1 to 3.

Suitable alkyl and aryl groups represented by $R^1$ include methyl, ethyl, propyl, butyl, and phenyl. Inter alia, methyl and ethyl are preferred.

Suitable alkyl and aryl groups represented by $R^2$ include methyl, ethyl, propyl, butyl, and phenyl. Inter alia, methyl and ethyl are preferred.

Suitable divalent hydrocarbon groups represented by A are alkylene groups including methylene, ethylene, propylene, butylene, pentylene, hexylene, octylene, and decylene, with hexylene being preferred.

Suitable divalent hydrocarbon groups represented by B are alkylene groups including methylene, ethylene, propylene, butylene, pentylene, hexylene, octylene, and decylene, with propylene being preferred.

The preferred organosilicon compound has the general formula (2).

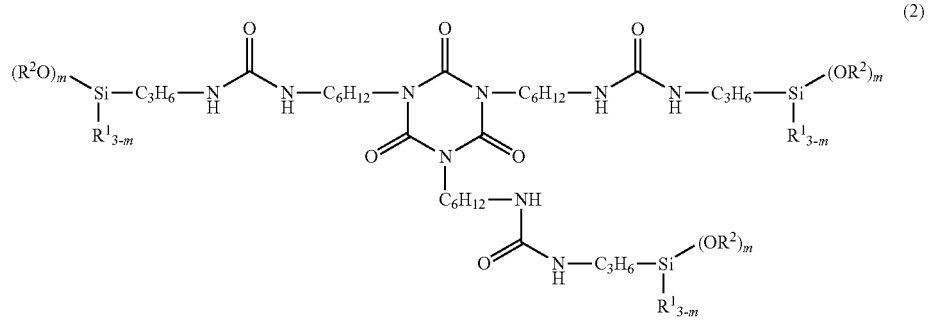

(2)

Herein $R^1$, $R^2$, and m are as defined above.

More preferred are organosilicon compounds having the formulae (3) and (4).

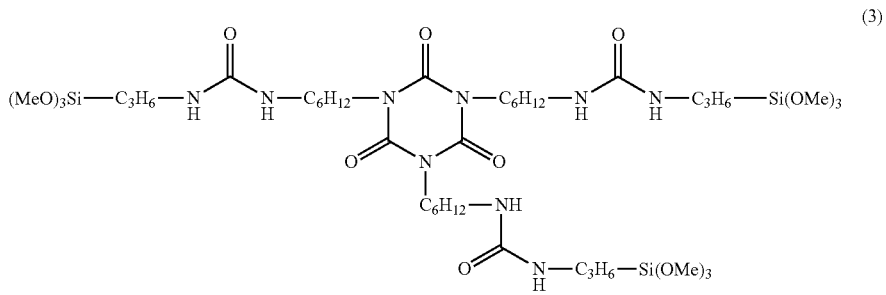

(3)

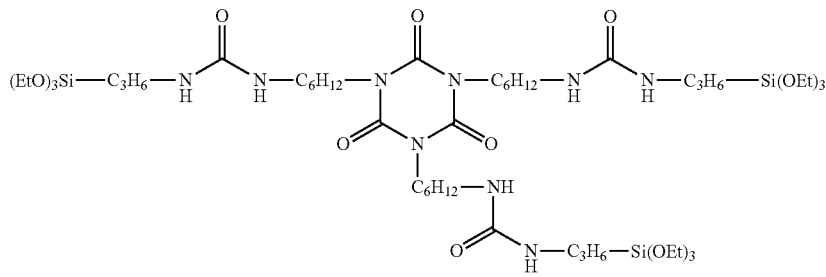

(4)

Since the organosilicon compounds mentioned above are solid at normal temperature, they may be added to powder coating compositions. Specifically, the organosilicon compound of formula (3) has a melting point of 120° C., and the organosilicon compound of formula (4) has a melting point of 115° C. By adding the organosilicon compound to a powder coating composition, the composition is improved in adhesion to substrates.

An appropriate amount of the organosilicon compound (A) added is 0.01 to 20 parts, more preferably 0.1 to 5 parts by weight, provided that the powder coating composition is 100 parts by weight. With less than 0.01 pbw of the organosilicon compound, water-loading resistant performance may be no longer improved. In excess of 20 pbw, the performance improvement may be saturated.

The powder coating composition is based on a resin, which may be selected from those resins commonly used in prior art powder coating compositions. Suitable resins include epoxy resins, polyester resins, epoxy-polyester resins, acrylic resins, fluoro-resins and silicone resins. Inter alia, (B) a carboxyl-containing resin is preferred. Included are carboxyl-containing polyester resins, carboxyl-containing acrylic resins, carboxyl-containing fluoro-resins, and carboxyl-containing silicone resins. Inter alia, carboxyl-containing polyester resins are especially preferred for processability and cost.

Suitable carboxyl-containing polyester resins include those resins obtained from reaction of an aromatic or alicyclic dicarboxylic acid such as phthalic acid (anhydride), isophthalic acid, terephthalic acid, dimethyl isophthalate, dimethyl terephthalate, hexahydrophthalic acid (anhydride) or tetrahydrophthalic acid (anhydride) with a dihydric alcohol such as (poly)ethylene glycol, (poly)propylene glycol, butylene glycol, neopentyl glycol, 1,6-hexanediol, or dimethylolpropionic acid, and optionally, further with a monocarboxylic acid such as benzoic acid, a tri- or polyfunctional carboxylic acid such as trimellitic acid (anhydride), or a tri- or polyhydric alcohol such as trimethylol ethane, trimethylol propane, glycerol or pentaerythritol, such that the acid residue may be left behind.

An appropriate amount of the resin, especially carboxyl-containing polyester resin (B) used is 7 to 99 parts, more preferably 15 to 95 parts by weight, provided that the powder coating composition is 100 parts by weight. A composition with less than 7 pbw of the resin may be poor in impact resistance and cupping resistance whereas a composition with more than 99 pbw of the resin may be less curable.

In a preferred embodiment, (C) a hydroxylalkylamide compound as curing agent is added to the powder coating composition. Among others, hydroxylalkylamide compounds having at least two functional groups per molecule are especially preferred when low-temperature curing behavior and properties of a cured coating are taken into account. Exemplary compounds are N,N,N',N'-tetrakis(2-hydroxyethyl)adipamide and N,N,N',N'-tetrakis(2-hydroxypropyl)adipamide.

An appropriate amount of the hydroxylalkylamide compound (C) used is 0.5 to 45 parts, more preferably 1 to 25 parts by weight, provided that the powder coating composition is 100 parts by weight. A composition with less than 0.5 pbw of compound (C) may be less curable whereas a composition with more than 45 pbw of compound (C) may be poor in impact resistance and cupping resistance.

To the powder coating composition, any additives such as fillers, coloring pigments, glitters, flow modifiers, aesthetic microparticulate polymers, surface modifiers, cure accelerators, and lubricants may be added, if desired.

On use of the powder coating composition, it may be applied to a substrate by an electrostatic powder coating technique using an electrostatic powder sprayer or triboelectric coater, typically to a thickness of 200 to 300 μm, more preferably 30 to 150 μm. The coating is baked typically at a (substrate) temperature of 140 to 230° C. for 2 to 60 minutes.

The powder coating composition may be applied to any substrates commonly used in the art. Examples of the substrate include metal substrates of steel, zinc, aluminum, copper and tin, surface-treated metal substrates, and metal substrates having an undercoat such as primer or intermediate coat. The composition finds applications in a variety of fields including vehicles, electric appliances, building parts, road-related parts, and business machines.

EXAMPLE

Examples of the invention are given below by way of illustration and not by way of limitation. All parts are by weight (pbw).
Synthesis of Organosilicon Compounds
Organosilicon Compound #1

A 1-L separable flask equipped with a stirrer, reflux condenser, dropping funnel and thermometer was charged with 91.3 g of a nurate-modified hexamethylene diisocyanate (Duranate® TPA-100 by Asahi Chemical Industry Co., Ltd.) and 200 g of toluene, to which 89.7 g (0.5 mol) of 3-aminopropyltrimethoxysilane (KBM-903 by Shin-Etsu Chemical Co., Ltd.) was added dropwise at an internal temperature of 100-110° C. over 10 minutes. Stirring was continued at 110° C. for 1 hour. Subsequent stripping yielded an organosilicon compound having a melting point of 120° C. On analysis by $^1$H-NMR spectroscopy, the reaction product was identified to be a compound having the structure of the following formula (3). This is designated Organosilicon compound #1.

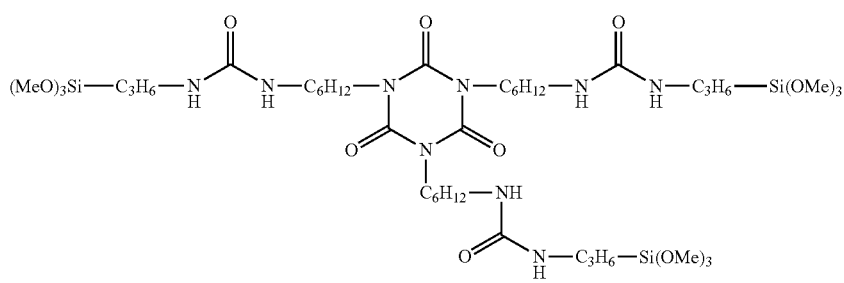

(3)

Organosilicon Compound #2

A 1-L separable flask equipped with a stirrer, reflux condenser, dropping funnel and thermometer was charged with 91.3 g of a nurate-modified hexamethylene diisocyanate (Duranate® TPA-100 by Asahi Chemical Industry Co., Ltd.) and 200 g of toluene, to which 110.7 g (0.5 mol) of 3-aminopropyltriethoxysilane (KBE-903 by Shin-Etsu Chemical Co., Ltd.) was added dropwise at an internal temperature of 100-110° C. over 10 minutes. Stirring was continued at 110° C. for 1 hour. Subsequent stripping yielded an organosilicon compound having a melting point of 115° C. On analysis by $^1$H-NMR spectroscopy, the reaction product was identified to be a compound having the structure of the following formula (4). This is designated Organosilicon compound #2.

was coated onto a substrate (SPCC steel plate of 0.8 mm thick treated with zinc phosphate Parbond #3118 by Nihon Parkerizing Co., Ltd.) in such a coating weight as to give a cured thickness of 60 µm, and baked and dried under such conditions as to keep the substrate temperature at 150° C. for 20 minutes, completing a coated plate (test sample). The test sample was examined for coating properties, with the results shown in Table 1.

[Gloss (60° G)]
measured according to JIS K-5600 4.7 (reflection 60 deg.)

[Impact Test]
According to JIS K-5400 8.3.2 Dupont impact test, an impact was applied to the coated surface and back surface of the coated plate under conditions including a drop weight of 1,000 g, an impact tip diameter of ½ inch, and a dropping

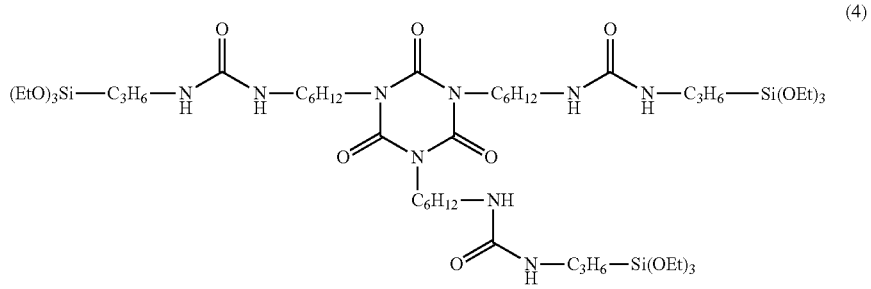

(4)

Examples 1 to 8 and Comparative Examples 1 to 2

A powder coating composition of the formulation (pbw) shown in Table 1 was admitted into a mixer (trade name High-Speed Mixer by Fukae Industry Co., Ltd., volume 2 L), where the contents were uniformly mixed for 1 minutes by rotating the agitator at 500 rpm and the chopper at 4,000 rpm. The mixture was melt kneaded on an extruder/kneader (trade name Buss Ko-Kneader PR46 by Buss) at a temperature of 80-120° C. The mass was cooled, finely ground on a hammer mill and sieved through a 200-mesh screen, obtaining a powder (coating composition) having an average particle size of 35 µm.

Polyester resin 1: M-8961 (DIC Corp., carboxyl-containing polyester resin)
Polyester resin 2: M-8962 (DIC Corp., carboxyl-containing polyester resin)
Curing agent: PRIMID XL-552 (EMS Griltech, β-hydroxyalkylamide)
Titanium oxide: JA-1 (Tayca Co., Ltd.)
Leveling agent: Resiflow® P-67 (Estron Chemical)
Using an electrostatic coating machine (trade name PG-1, Matsuo Sangyo Co., Ltd.), the powder coating composition height of 50 cm. Pressure-sensitive adhesive tape (cellophane tape) was attached to the impacted area and instantly pulled back. It was examined how the coating was stripped.
○: no stripping of coating observed
Δ: some stripping of coating observed
x: noticeable stripping of coating observed

[Cross-Hatch Adhesion]
measured according to JIS K-5600 5.6

[Boiling Water Resistance, Outer Appearance]
The test sample was immersed in boiling water for 2 hours before the coating was visually inspected for outer appearance.
○: gloss maintained
Δ: a lowering of gloss, matting
x: a substantial loss of gloss

[Boiling Water Resistance, Cross-Hatch Adhesion]
The test sample was immersed in boiling water for 2 hours before it was evaluated according to JIS K-5600 5.6.

[Moisture Resistance, Outer Appearance]
The test sample was subjected to 500-hour continuous test according to JIS K-5400 9.2.2 before it was visually inspected.

○: gloss maintained
Δ: a lowering of gloss, matting
x: a substantial loss of gloss

[Moisture Resistance, Cross-Hatch Adhesion]

The test sample was subjected to 500-hour continuous test according to JIS K-5400 9.2.2 before it was evaluated according to JIS K-5600 5.6.

[Salt Water Spraying, Cut Stripping]

The test sample was cross-cut on its coated surface and subjected to 500-hour salt water spraying according to JIS K-5400 9.2. Adhesive tape was attached to the cut area and pulled back. Stripping distance is the maximum of width of a stripped portion of coating from the center line between cut lines.

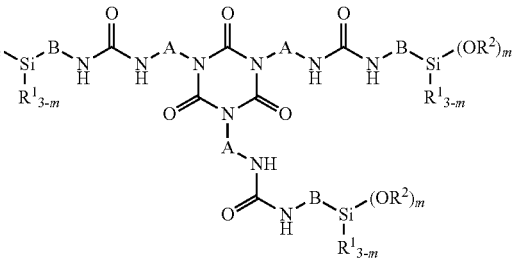
(1)

TABLE 1

| Formulation (pbw) | Example | | | | | | | | Comparative Example | |
|---|---|---|---|---|---|---|---|---|---|---|
| | 1 | 2 | 3 | 4 | 5 | 6 | 7 | 8 | 1 | 2 |
| Polyester resin 1 | 65 | 65 | | | 65 | 65 | | | 65 | |
| Polyester resin 2 | | | 65 | 65 | | | 65 | 65 | | 65 |
| Organosilicon compound #1 | 1 | 3 | 1 | 3 | | | | | | |
| Organosilicon compound #2 | | | | | 1 | 3 | 1 | 3 | | |
| Curing agent | 5 | 5 | 5 | 5 | 5 | 5 | 5 | 5 | 5 | 5 |
| Benzoin | 0.2 | 0.2 | 0.2 | 0.2 | 0.2 | 0.2 | 0.2 | 0.2 | 0.2 | 0.2 |
| Titanium oxide | 30 | 30 | 30 | 30 | 30 | 30 | 30 | 30 | 30 | 30 |
| Leveling agent | 0.5 | 0.5 | 0.5 | 0.5 | 0.5 | 0.5 | 0.5 | 0.5 | 0.5 | 0.5 |
| Test results | | | | | | | | | | |
| Gloss (60° G) | 94 | 95 | 95 | 95 | 94 | 95 | 95 | 94 | 95 | 94 |
| Impact test | ○ | ○ | ○ | ○ | ○ | ○ | ○ | ○ | ○ | ○ |
| Cross-hatch adhesion | 100/100 | 100/100 | 100/100 | 100/100 | 100/100 | 100/100 | 100/100 | 100/100 | 100/100 | 100/100 |
| Boiling water resistance, outer appearance | ○ | ○ | ○ | ○ | ○ | ○ | ○ | ○ | X | X |
| Boiling water resistance, cross-hatch adhesion | 100/100 | 100/100 | 100/100 | 100/100 | 100/100 | 100/100 | 100/100 | 100/100 | 50/100 | 50/100 |
| Moisture resistance, outer appearance | ○ | ○ | ○ | ○ | ○ | ○ | ○ | ○ | X | X |
| Moisture resistance, cross-hatch adhesion | 100/100 | 100/100 | 100/100 | 100/100 | 100/100 | 100/100 | 100/100 | 100/100 | 20/100 | 20/100 |
| Salt water spraying, cut stripping (mm) | 2.2 | 2.4 | 2.1 | 2.2 | 2.2 | 2.3 | 2.0 | 2.2 | 3.0 | 3.1 |

Japanese Patent Application No. 2015-135344 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A powder coating composition comprising (A) an organosilicon compound having the general formula (1):

wherein $R^1$ is each independently a $C_1$-$C_{10}$ alkyl or $C_6$-$C_{10}$ aryl group, $R^2$ is each independently a $C_1$-$C_{10}$ alkyl or $C_6$-$C_{10}$ aryl group, A is a $C_1$-$C_{20}$ divalent hydrocarbon group, B is a $C_1$-$C_{20}$ divalent hydrocarbon group, and m is an integer of 1 to 3, and (B) a resin selected from the group consisting of epoxy resins, polyester resins, epoxy-polyester resins, acrylic resins, fluoro-resins, and silicone resins, wherein the organosilicon compound is contained in an amount of 0.1 to 5 parts by weight, provided that the powder coating composition is 100 parts by weight.

2. The powder coating composition of claim 1 wherein the organosilicon compound has the general formula (2):

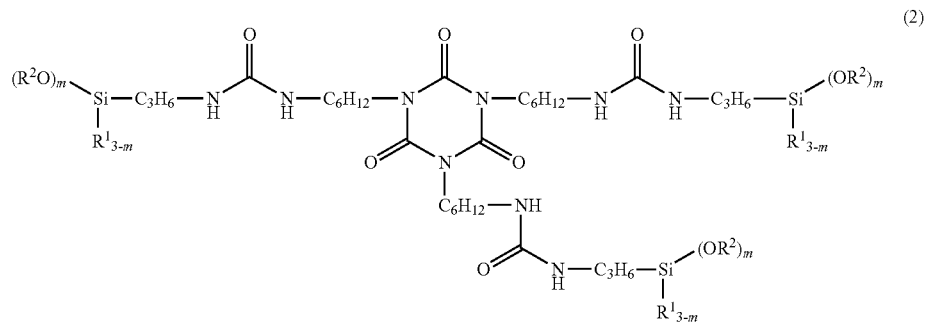

wherein $R^1$, $R^2$, and m are as defined above.

3. The powder coating composition of claim 1, wherein resin component (B) comprises a carboxyl-containing polyester resin.

4. The powder coating composition of claim 1, further comprising (C) a β-hydroxyalkylamide compound.

5. A coated article obtained by coating a substrate with the powder coating composition of claim 1.

* * * * *